United States Patent [19]

Huck et al.

[11] 4,278,089

[45] Jul. 14, 1981

[54] WOUND DRAINAGE DEVICE

[75] Inventors: Charles M. Huck, Oldwick; John E. Studer, Flemington, both of N.J.; Philip H. Sauer, Indian Rocks Beach, Fla.

[73] Assignee: Howmedica, Inc., New York, N.Y.

[21] Appl. No.: 959,161

[22] Filed: Nov. 9, 1978

[51] Int. Cl.³ .............................................. A61M 1/00
[52] U.S. Cl. .................................... 128/278; 417/328; 417/472; 141/26; 141/67; 128/760; 128/766
[58] Field of Search ............... 128/276, 278, 752, 753, 128/754, 760, 765, 766, 767, 277; 417/472, 328; 141/25, 26, 67; 222/386.5; 92/17, 23, 40, 43, 44

[56] References Cited

U.S. PATENT DOCUMENTS

| | | | |
|---|---|---|---|
| 799,297 | 9/1905 | Betzler | 401/153 |
| 2,074,223 | 3/1937 | Horiuchi | 128/278 |
| 2,595,493 | 5/1952 | Slaby et al. | 128/276 |
| 3,115,138 | 12/1963 | McElvenny et al. | 128/278 |
| 3,376,868 | 4/1968 | Mondiadis | 128/278 |
| 3,416,431 | 12/1968 | Hitzeroth | 267/156 |
| 3,421,662 | 1/1969 | Hanson | 222/95 |
| 3,680,560 | 8/1972 | Pannier et al. | 128/276 |
| 3,742,952 | 7/1973 | Magers | 128/278 |
| 3,774,611 | 11/1973 | Tusey et al. | 128/278 |
| 3,779,243 | 12/1973 | Tusey et al. | 128/278 |
| 3,809,086 | 5/1974 | Schachet | 128/278 |
| 3,809,087 | 5/1974 | Lewis, Jr. | 128/278 |
| 3,871,554 | 3/1975 | Huck | 222/96 |
| 3,875,941 | 4/1975 | Adair | 128/278 |
| 4,136,802 | 1/1979 | Mascia et al. | 92/40 |

FOREIGN PATENT DOCUMENTS

| | | |
|---|---|---|
| 879849 | 8/1971 | Canada . |
| 1282856 | 11/1968 | Fed. Rep. of Germany . |
| 1810801 | 6/1970 | Fed. Rep. of Germany . |
| 1239249 | 7/1960 | France .................................. 417/472 |
| 939529 | 10/1963 | United Kingdom . |
| 1304324 | 1/1973 | United Kingdom . |
| 1400139 | 7/1975 | United Kingdom . |

*Primary Examiner*—Robert W. Michell
*Assistant Examiner*—J. L. Kruter
*Attorney, Agent, or Firm*—Pennie & Edmonds

[57] ABSTRACT

A device for removing fluids from a wound includes a housing and a passive bellows inside the housing. The bellows can be collapsed and retained in a collapsed or activated state. Upon release from its activated state, the bellows is expanded so as to provide a substantially constant level of negative pressure whereupon fluids from a wound are automatically drawn into and collected within the bellows at a substantially constant rate of suction throughout the range of evacuation. Preferably the bellows is expanded by a constant force ribbon spring which provides a constant force of expansion. Additionally, the housing is preferably transparent with graduations etched thereon permitting the visible inspection and measurement of the fluids removed from the wound.

17 Claims, 8 Drawing Figures

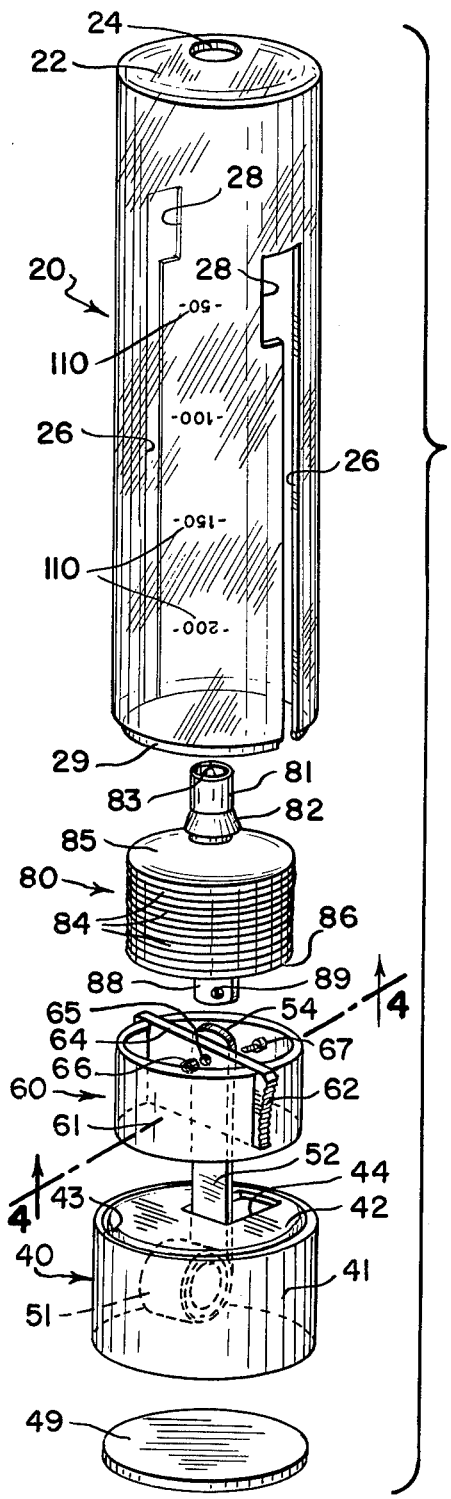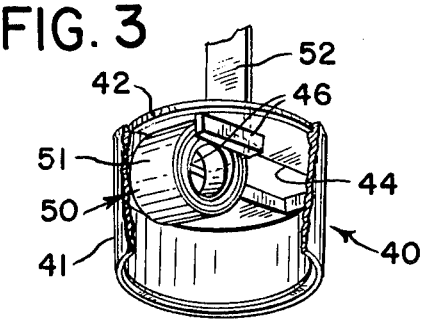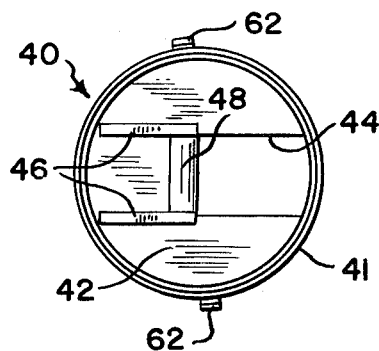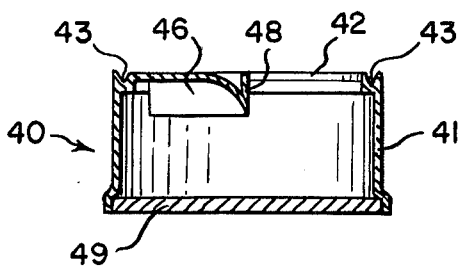

WOUND DRAINAGE DEVICE

TECHNICAL FIELD

This invention relates to suction devices and more particularly to an improved device for automatic removal of fluids from a wound.

BACKGROUND ART

The use of suction devices to remove fluids from a wound is known to the art. Such devices are employed to reduce or remove the body fluids which normally collect at a wound site after surgery.

Body fluids which collect at a wound, if left to remain especially in a closed wound, may cause complications in the healing process and thereby reduce the chance of a successful convalescence. Moreover, not only will a dry wound area accelerate the healing stage but will also promote cicatrization.

Known typical suction devices are both disclosed and illustrated in Canadian Pat. No. 879,849; British Pat. No. 1,304,324 to Astra-Meditec; British Pat. No. 1,400,139 to Mathys; U.S. Pat. No. 3,115,138 to McElvenny et al.; U.S. Pat. No. 3,376,868 to Mondiadis; U.S. Pat. No. 3,742,952 to Magers et al.; U.S. Pat. Nos. 3,774,611 and 3,779,249 to Tussey et al.; U.S. Pat. No. 3,809,086 to Schachet et al.; U.S. Pat. No. 3,809,087 to Lewis, Jr.; and U.S. Pat. No. 3,875,941 to Adair.

With reference to the Canadian patent, the device disclosed therein includes a container with a concertina-pleated wall that can be expanded to increase the volume of the container. A detachable external spring bow serves to extend the pleated wall thereby causing suction within the container. The concertina-pleated walls are consecutively numbered to permit measurement of the fluid collected when the container is in an open, extended position.

The Astra-Meditec patent discloses a bellows operated disposable aspiration drainage device. A non-return inlet valve permits the collection of body fluids into the bellows from an inlet catheter connected to the wound to be drained. The collected body fluids are discharged through a non-return outlet valve into a receiving bag. The latter is graduated to allow measurement of removed body fluids.

The Mathys patent discloses a suction drainage device which includes a resiliently compressible, airtight container having a watertight plastic bag detachably secured therein. The container upon expansion produces a negative pressure which results in the flow of body fluids into the bag within. A helical spring can be used inside the container to provide expansion of the container.

The McElvenny patent discloses an evacuator that includes a fluid tight container. After manual compression, the container is expansible to provide suction either by means of internally positioned springs between additional members placed within the container or by virtue of the container being constructed of resilient material.

The evacuator disclosed in the Mondiadis patent includes a compressible container made from resilient elastomeric material whose memory causes the walls to return to an uncompressed state. A valve turret on the top of the container provides both an inlet and a vent opening which is sealable by means such as a plug or a resilient diaphragm connected to the top.

The Magers et al. patent discloses a surgical suction assembly including a suction container which is resiliently compressible and expansible. A one way plug is provided to admit fluid into the container while drawing fluid and to block flow outwardly therefrom.

The Tussey '611 patent discloses a contamination free evacuator including a compressible-expandable container having an inlet and an outlet region, and a fluid stabilizer inside the container.

A contamination free evacuator is also disclosed in the Tussey '243 patent which includes a compressible and expandable evacuator bag having both a drain inlet and an exhaust outlet formed in the bag. The latter further includes a magnetic one-way exhaust valve which prevents the contamination of the bag by closing upon completion of exhausting fluids from the bag.

The Schachet et al. patent is directed to a wound suction device including a vessel having therein an elastic sheet diaphragm which is sealed to the walls of the vessel. Movement of the diaphragm by a plate with an actuating means decreases the volume of the vessel which results in the creation of a suction force upon release of the actuating means. Provision is made to lock the actuator means in a position such that the resilient diaphragm remains displaced.

In the Lewis patent, a suction apparatus is disclosed having a collapsible bag attached at opposed surfaces to plate members one of which is biased to move away from the other plate member. Disclosed biasing means include springs and rubber bands.

The evacuating system disclosed in the Adair patent includes a bellows-type container having resilient accordian-like sidewalls made of an elastomeric material. Initial suction of the container is provided by the resilient accordian-like sidewalls. Further suction results from the added weight of collected fluid within the container. Operation of this system requires that the bellows-type container be mounted in a vertical position with evacuating tubing attached to the top portion of the container.

Although each of the above-mentioned patented devices is useful in varying degrees, they all suffer from some of several disadvantages which include, e.g., the necessity of activation just prior to use, the lack of ease in operation, the need of resilient containers or component members, complex structure, and the inability to maintain a substantially constant level of negative pressure.

All of the above patents except Schachet provide no disclosure of a device which can be received by the handler in a preactivated or compressed state. These devices require that the handler collapse the bellows or container to activate the device before use. Difficulty in operation is presented particularly in the Astra-Meditec apparatus, the Canadian drain, and the Adair device. The Astra-Meditec apparatus discloses a directional multicomponent valve system which requires that the handler properly connect the device to the wound and the collecting bag. Multi-component complex valve arrangements are also disclosed in the Magers valve means and the Tussey '243 magnetic exhaust valve. The Canadian drain not only requires that the user compress the concertina-pleated walls to drain air from the device but also that an external spring bow be attached further complicating the operation thereof. In the Adair device, difficulty arises from the requirements that the device be maintained upright for proper operation. Increased cost of operation or construction results from the multicomponent or complex valve systems disclosed in the Astra-Meditec, Magers, and Tussey '243 patents; and from the need of additional collecting bags in the Astra-Meditec and Mathys patents. Resilient retaining containers or component members are disclosed in one form or another in most of the above patents. Complex structure is formed in the multiple spring arrangement disclosures of the McElvenny, Tussey '243, and Lewis patents, and in the need of a fluid stabilizer as disclosed in the Tussey '611 patents. Such complex structures complicate construction as well as increase the cost thereof. Finally, none of the above patents disclose a device providing substantially constant suction over the range of operation. The spring means disclosed in the Canadian, Mathys, McElvenny, Tussey '243, and the Lewis device do not allow for a substantially constant suction operation.

DISCLOSURE OF INVENTION

The device of the present invention is intended to improve over the apparatus discussed above and to overcome the limitations found therein. The device of the present invention is designed to provide a substantially constant flow rate throughout the range of drawing and collecting body fluids from a wound into the device. Also the device is available to the user in a preactivated state. The device thus avoids the need for the handler to discharge the air within the device as is found to be the case with almost all of the apparatus of the above discussed prior art. Additional ease of operation is provided herein in that this device permits one hand operation freeing the handler to attend to additional matters while simultaneously activating the device. The device is also designed to permit alternatively either total discard or evacuation of the collected fluids and reactivation for subsequent reuse.

The device of the present invention comprises a substantially rigid housing with an end wall and an opening therein at one end. Inside the housing is an airtight and watertight passive container which collects the body fluids. A means is provided to allow communication between the inside of the container and outside of the housing. Means are also provided to maintain the passive container adjacent the housing cover thus allowing a substantially fixed point from which the passive container expands. Other means provide for the collapsing and retaining of the passive container in a collapsed state. A means external to the passive container provides for automatic expansion of the passive container to provide a constant rate of suction. In one preferred embodiment of the present invention, the container is a passive bellows and the expansion means is a constant force spring assembly.

Accordingly, it is an object of the present invention to provide a wound suction device having an expansion means that provides a substantially constant suction over the range of evacuation.

Another object of the present invention is to provide a wound suction device that may be used easily with one hand.

Still another object of the present invention is to provide a wound suction device that is inexpensive and totally discardable.

Yet still another object is to provide a wound suction device that may be evacuated and reactivated for subsequent reuse.

A further object of the present invention is to provide a device that is available to a user in a preactivated or compressed state.

BRIEF DESCRIPTION OF DRAWINGS

FIG. 2 is an exploded view of the device according to FIG. 1.

FIG. 3 is a cutaway perspective view of a base of the device of FIG. 2 housing a constant force spring assembly.

FIG. 4a is a bottom view of the base of FIG. 3.

FIG. 4b is a cross-sectional view of the base of assembly FIG. 3 along line 4—4 in FIG. 2.

FIG. 6b is a top view of the slide collar of FIG. 6a.

BEST MODE FOR CARRYING OUT THE INVENTION

Figure 1:
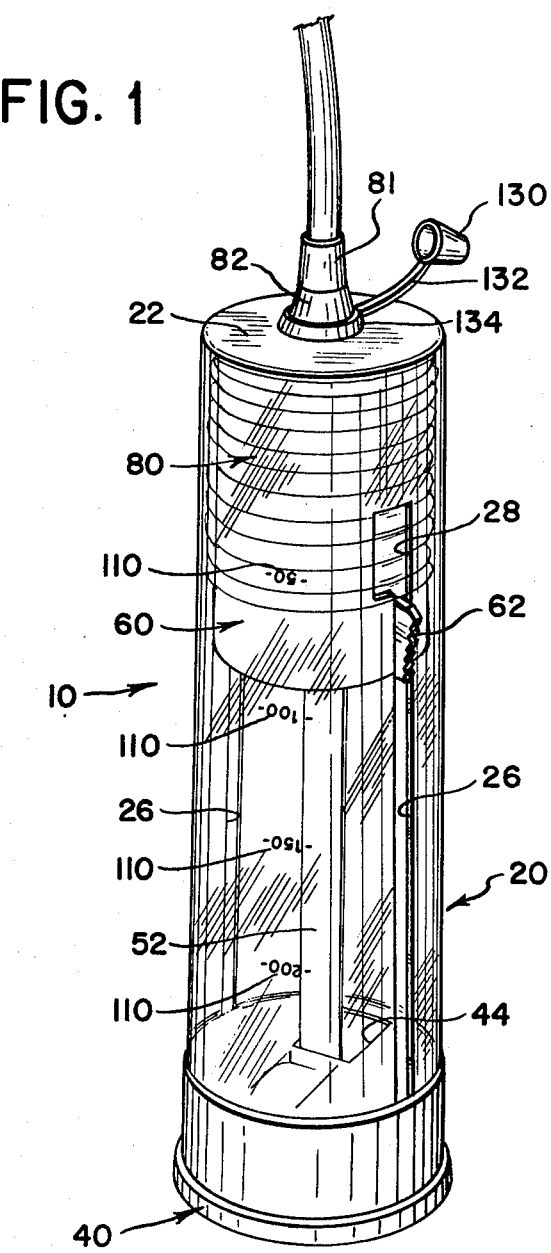
FIG. 1 is a perspective view of a device according to the present invention.

FIG. 1 illustrates the device 10 according to the present invention.

FIG. 2 provides an exploded view of the device 10 thereby illustrating the component parts and structure and assembly thereof. Generally the device 10 comprises a substantially rigid cylindrical housing 20 closed at one end and open at the other end, and enclosing in sequence from the closed end a passive bellows 80, a slide collar 60, and a base 40 which is fixedly mated to the open end of the housing 20. A constant force spring assembly 50 is housed within the base 40. Both the spring assembly 50 and the bellows 80 are attached to the slide collar 60. Thereby the bellows 80 is expanded or kept constantly expanding by the force provided by the spring assembly 50.

The cylindrical housing 20 of the device 10 has an integral end wall 22 at the closed end thereof. The end wall 22 has an opening 24 which permits communication with the bellows 80 within the housing 20. Two slits 26 are oppositely positioned in the side walls of the housing 20 and are substantially aligned with the longitudinal axis of the housing 20. The slits 26 run from a first position to a second position coincident with the other end of the housing 20. The slits 26 at the first position include cutouts 28 as shown in FIGS. 1 and 2. The purpose of these slits 26 and cutouts 28 will be made evident in the description to follow. The other end of the housing 20 terminates integrally in a ring 29 which has an outside diameter less than the outside diameter of the housing 20.

The bellows 80 has an upper end 85 and a lower end 86. The bellows 80 is disposed within the housing with its upper end 85 adjacent the end wall 22. The bellows 80 has ribbed portions 84 which permit the bellows 80 to expand to increase the volumetric capacity. At the lower end 86 of the bellows 80 is an appendage 88 with opening 89 therein which, as will be described herein, permits coupling of the bellows 80 with the remaining structure within the housing 20. Integral with the upper end 85 and communicating with the interior of the bellows 80 is a tube 81. The tube 81 has circumferentially thereon a flange 82 having a frusto-conical shape which permits passage of the tube 81 through the end wall opening 24 but which does not allow the tube 81 to be withdrawn back through the opening 24. In this manner the upper end 85 of the bellows 80 is kept adjacent the end wall 22. The bellows 80 can then be expanded downward toward the other end of the housing 20.

Also enclosed within the housing 20 is a slide collar 60 which comprises an annular ring 61 that slides within the housing 20. The longitudinal axis of annular ring 61 is aligned with that of the housing 20. The slide collar 60 includes a cross bar 64 which is disposed along one diameter of the annular ring 61 in slots (not shown) and extends beyond that one diameter to opposite tabs 62. These tabs 62 when engaged within the slits 26 protrude beyond the side walls of the housing 20. The tabs 62 are shaved at an angle toward the base 40 and are ribbed so that they may be easily engaged by the fingers. The cross bar 64 also has a first opening 65 and a second opening (not shown) positioned beneath the first opening 65. By means of opening 65, the bellows 80 can be attached to the slide collar 60. After aligning opening 89 of the bellows 80 with opening 65, a bolt 67 passes through bellows opening 85, cross bar opening 65, and is engaged by nut 66 thereby attaching bellows 80 to the slide collar 60.

The base 40 comprises a generally cylindrical side wall structure 41 with an integral top end wall 42. The top end wall 42 has a generally rectangular opening 44 and on its underside are two generally parallelly positioned ribs 46 as shown in FIGS. 3, 4a and 4b, and a curved wedge 48 particularly shown in FIG. 4b disposed between the ends of the ribs 46 and adjacent one end of generally rectangular opening 44. The spring assembly 50 comprises a coiled spring 51 a portion of which is confined in the space defined by the ribs 46 as shown in FIG. 3. The coiled portion 51 of the spring assembly 50 is housed between the ribs 46 and against wedge 48. The uncoiled or free portion 52 of the spring assembly 50 extends through the top end wall 42 opening 44 and terminates at a free end 54 with an opening (not shown) thereat which permits the attachment of the spring assembly 50 to the slide collar 60 after alignment with the second opening (not shown) of the cross bar 64 via a bolt and nut (both not shown) in the same manner that the bellows 80 was attached to the slide collar 60. The top end wall 42 has circumferentially within its upper edge a groove 43 adapted to matably receive the housing ring 29. A bottom end wall 49 seals the spring assembly 50 within the base 40.

After the bellows 80 and base 40 are each attached as described above to the slide collar 60, assembly of the device 10 is accomplished by inserting the above-mentioned components bellows 80 first within the housing 20 so that the tabs 62 are slidably engaged within slits 26. The bellows 80 is inserted tube 81 first. Once the flange 82 of the tube 81 passes through the end wall opening 24, the tube 81 cannot pass back into the housing 20. In addition, the upper end of the bellows 80 is thus kept adjacent the cover 22 and thus serves as a fixed point from which the bellows 80 will expand by means of the force of spring assembly 50. Assembly is completed when the base 40 is fixed to the housing 20 by means of fitting housing ring 29 into base groove 43. When the tabs 62 are advanced to the first position or slide into the housing 20 as far as possible, a slight twisting of the tabs 62 into the cutouts 28, dimensioned to at least partially receive the tabs 62 as shown in FIG. 2, will lock the tabs 62 in place and expand spring assembly 50. The first position of the slits 26 is preferably chosen so that the bellows 80 is fully collapsed when the tabs 62 are so engaged within the cutouts 28. Upon release of the tabs 62 from their locked positions within cutouts 28, the force of the spring assembly 50 will automatically draw the slide collar 60 without further action on the part of the user, toward the other end of the housing 20 and will simultaneously automatically expand the bellows 80 which is attached to the slide collar 60 thereby producing a negative pressure within the bellows 80.

Figure 5:
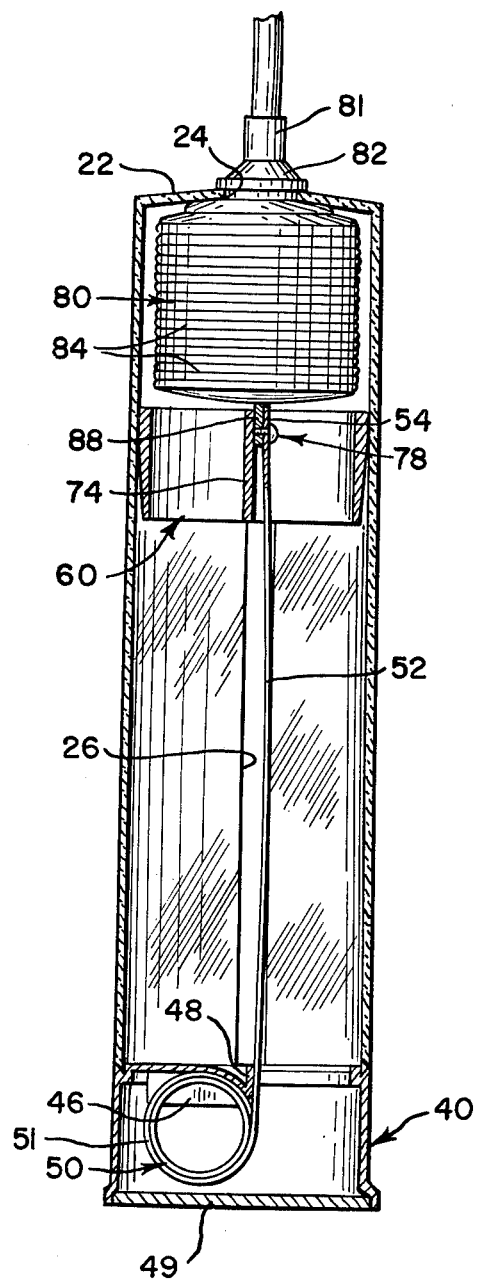
FIG. 5 is a cross-sectional view of the device of FIG. 1 along line 4—4 in FIG. 2.

FIG. 5, a vertical cross-sectional view along line 4—4 in FIG. 2, illustrates the positions of the component structure of the device 10 when the bellows 80 is in a collapsed or preactivated state within the housing 20.

Figure 6A:
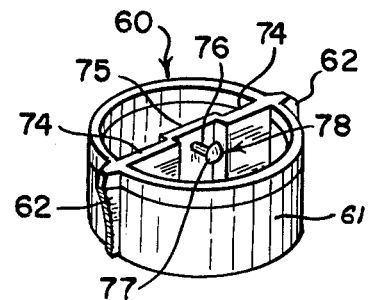
FIG. 6a is a perspective view of a slide collar of the device of FIG. 5.
Figure 6B:
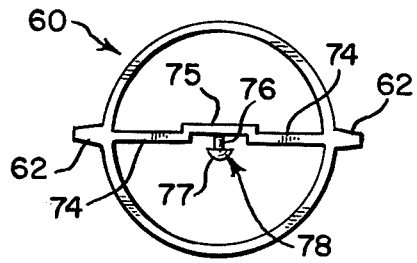

FIGS. 6a and 6b illustrate another embodiment of the slide collar 60. The cross bar 74 has a recessed portion 75 which is of suitable dimension to receive the free end 54 of the spring assembly 50. Within the recessed portion 75 is a knob 78 having a shank 76 and enlarged head 77. Both the bellows 80 and spring free end 54 are attached to the slide collar 60 by engaging the bellows opening 89 and the spring free end opening (not shown) over the enlarged head 77 and onto the shank 76 as shown in FIG. 5. The force supplied by the spring assembly 50 maintains the bellows 80 and the spring free end 54 fixed to the slide collar 60.

The assembly of the device 10 may be finalized by the gluing of separate structural components together. Preferably the ring 29 of the other end of housing 20 is glued into the groove 43 on the upperside of the integral base top end wall 42. The cross bar 64 can also be glued into its cutouts (not shown) in the annular ring 61 of slide collar 60. Alternatively, the end walls 22 and 42, and tube 81 can be constructed separately from their respective structures and glued thereto. In a preferred assembly, ultrasonic welding is used to attach the ring 29 to the groove 43. Assembly of the device 10 is not limited to gluing and ultrasonic welding but may be accomplished by other conventional means known and appreciated by those skilled in such arts including but not limited to mechanical means such as screws.

Preferably the housing 20 will be made of a transparent plastic and will have etched graduations 110 thereon as shown in FIG. 1. The user will therefore be able to visibly inspect the proper operation of the device 10. Additionally he can measure the amount of fluid collected upon holding the housing 20 bellows upper end 85 down and comparing the fluid level against the graduations 110.

The device 10 can be supplied with a protective wrapping (not shown) to prevent inadvertent release of tabs 62 from their locked position while the bellows 80 is in a preactivated state. The wrapping can also serve to provide user or other desired information printed thereon. Additionally information may be imprinted on the base bottom end wall 49 by the user to identify the patient and other pertinent data relevant to the particular usage of the device 10.

Preferably the bellows 80, base 40, slide collar 60, and tube 81 are made by injection molding of suitable plastic material.

Advantageously the housing 20 is substantially rigid thereby avoiding the possibility of inadvertent compression by a patient rolling over onto the device 10.

The bellows tube 81 can be supplied, if desired, with a cap 130 as shown in FIG. 1. The cap 130 preferably is connected via a strand 132 attached to the circumference of ring 134 which is adapted to be press fitted over flange 82. In this fashion, the tube 81 can be covered at its outer end by the cap to maintain a sterile environment within the bellows 80 prior to use or to seal the fluids within the bellows 80 after use.

The bellows tube 81 can alternatively be supplied, if desired, with a conventional Y connector (not shown). One duct of the conventional Y connector would be connected to the tube 81. Another duct would be connected via conventional urethane tubing to an additional Y connector (not shown) which would also be connected to wound tubing (not shown) having one end disposed in the wound. A conventional non-return valve (not shown) could be inserted at some position along the tubing configuration. The remaining duct of the Y connector connected to the tube 81 would have a cap (not shown) arranged similarly to cap 130, strand 132, and ring 134 for tube 81. Normally this cap would seal the remaining duct while fluid is drawn from the wound through the conventional tubing and into the bellows 80. However, removal of the cap on the remaining Y connector duct permits evacuation of fluid from the bellows 80 by advancing the tabs 62 toward the first position thereby compressing the bellows 80. Thus the fluid may be totally evacuated from the bellows 80 which then is ready for continued use or reuse, or partially into another container to permit immediate transfer of the fluid for study, e.g. in a pathology laboratory, without disrupting the hookup of the device 10 for further removal of fluid from a wound.

The device 10 is designed to permit either discarding of the entire unit, or reuse after evacuating the fluids therein. After complete evacuation, the bellows 80 may be cleansed and reactivated for further use, if desired, by means of the Y connector via the discharge procedure described above.

In the preferred embodiment, the spring assembly 50 is a constant force ribbon spring as shown in FIG. 3 and as disclosed and illustrated in U.S. Pat. Nos. 2,609,191; 2,609,192; and 2,609,193. Such springs are desirable since they have the feature of providing a nearly constant force throughout their range of expansion. In this manner, the device 10 provides a substantially constant suction throughout the range of evacuation, a feature found by most doctors to be quite desirable in such devices. Furthermore, such spring assemblies render the device 10 insensitive to orientation so that no particular orientation of the device 10 is required.

Other embodiments are possible with a constant force means different from the spring assembly 50 as disclosed. Moreover, different structure configurations are possible without departing from the scope of the invention, e.g., the bellows 80 may be fixed at the other end of the housing 20 and permitted to expand towards the housing end wall 22 with suitable tubing and force means.

We claim:

1. A device for removal of fluids from a wound comprising:
    a. a housing having side walls and at least one end wall at one end thereof, said end wall having an opening;
    b. an airtight and watertight passive bellows disposed within the housing, the passive bellows being collapsible and expandable and having an upper and a lower end;
    c. means for communicating with the interior of the passive bellows;
    d. means for maintaining the upper end of the passive bellows adjacent said end wall of the housing;
    e. means for collapsing the passive bellows within the housing; and
    f. constant force expansion means for automatically expanding the passive bellows from its collapsed state such that a substantially constant level of negative pressure is created within the passive bellows so as to provide for the removal of fluids from the wound at a substantially constant rate of suction throughout the range of evacuation, said expansion means including a constant force spring assembly being disposed outside the passive bellows and being secured to the housing and the passive bellows.

2. The device of claim 1 further including a means for retaining the passive bellows in a collapsed state.

3. A device for removal of fluids from a wound comprising:
    a. a housing having side walls and at least one end wall at one end thereof, said end wall having an opening;
    b. an airtight and watertight passive container disposed within the housing, the passive container being collapsible and expandable and having an upper and a lower end;
    c. means for communicating with the interior of the passive container, the communicating means including a hollow tube, said tube being integral with the upper end of the passive container and communicating therein, said tube extending through the opening of said end wall such that the interior of the passive container is in communication with the outside of the housing;
    d. means for maintaining the upper end of the passive container adjacent said end wall of the housing, the maintaining means including a flange disposed about the hollow tube and above the upper end of the passive container a distance at least slightly larger than the thickness of said end wall, said flange adapted to normally permit one-way passage of the hollow tube from within to without the housing through the opening of said end wall, such that the upper end of the passive container is kept disposed adjacent said end wall of the housing;
    e. means for collapsing the passive container within the housing; and
    f. means disposed outside the passive container for automatically expanding the passive container from its collapsed state so as to provide a substantially constant level of negative pressure within the passive container, thereby providing for the removal of fluids from the wound at a substantially constant rate of suction throughout the range of evacuation.

4. A device for removal of fluids from a wound comprising:
    a. a housing having side walls and at least one end wall at one end thereof, said end wall having an opening;
    b. an airtight and watertight passive bellows disposed within the housing, the passive bellows being collapsible and expandable and having an upper and a lower end;
    c. means for communicating with the interior of the passive bellows;
    d. means for maintaining the upper end of the passive bellows adjacent said end wall of the housing;
    e. means for collapsing the passive bellows within the housing;

f. means disposed outside the passive bellows for automatically expanding the passive bellows from its collapsed state so as to provide a substantially constant level of negative pressure within the passive bellows, thereby providing for the removal of fluids from the wound at a substantially constant rate of suction throughout the range of evacuation, the expansion means being a constant force spring assembly;

g. means for retaining the passive bellows in a collapsed state; and h. a base capable of being mated and attached to the other end of the housing.

5. The device according to claim 4 wherein the housing side walls are generally cylindrical.

6. The device according to claim 5 further including at least one slit of suitable width, said slit disposed in the side walls of the housing and aligned with the longitudinal axis of the housing, said slit extending from a first position adjacent the end wall to a second position adjacent the other end of the housing.

7. The device according to claim 6 wherein the collapsing means comprises a collar slidably engaged within the housing between the other end of the housing and the lower end of the passive bellows, said collar being attached to the lower end of the passive bellows, said collar having extending radially therefrom at least one tab, said tab being slidably engaged within and extending sufficiently beyond said slit, whereby movement of said tab toward the first position collapses the passive bellows.

8. The device according to claim 7 wherein the first position is suitably chosen so that the passive bellows is substantially fully collapsed when said tab is at the first position.

9. The device according to claim 8 wherein the retaining means comprises said slit having at least one cutout at the first position, said cutout suitably dimensioned to receive said tab when said tab is at the first position and twisted into the cutout, said cutout thereby retaining the tab and maintaining the passive bellows in a collapsed state.

10. The device according to claim 8 wherein the constant force spring assembly is housed within the base, said spring assembly having a free end extending along the longitudinal axis of the housing and attached to the collar, whereby release of said tab from its cutout allows the spring assembly to draw the collar toward the other end of the housing and thereby expand the passive bellows to produce a negative pressure therein.

11. The device according to claim 10 wherein the spring assembly is a constant force ribbon spring.

12. The device of claim 11 wherein the housing is substantially rigid.

13. The device according to claim 12 wherein the housing is a transparent plastic thereby permitting visible inspection of the operation of the passive bellows, the collar, and the spring assembly within the housing.

14. The device according to claim 13 wherein the passive bellows is a transparent plastic thereby permitting the visible inspection of the fluid therein from the wound.

15. The device according to claim 14 further including graduations on the housing thereby permitting the measuring of fluid withdrawn from the wound into the passive bellows.

16. A device for drawing fluids from a portion of a human body comprising:

a. a housing having at least one opening;

b. airtight and watertight passive container means disposed within the housing, the passive container means being collapsible and expandable and having its interior in communication with the opening in the housing;

c. constant force expansion means disposed outside the passive container means and secured to the housing for automatically expanding the passive container means from at least a partially collapsed state such that a substantially constant level of negative pressure is created within the passive container means so as to provide for the drawing of fluids therein from the portion of a body at a substantially constant rate of suction throughout the range of evacuation; and d. means for connecting the opening of the housing to the portion of the human body from which fluids are to be drawn.

17. A method for drawing fluids from a portion of a body comprising:

a. taking a suction device in a preactivated state, said device including a housing having at least one opening, airtight and watertight passive container means disposed within the housing, the passive container means being collapsible and expandable and having its interior in communication with the opening in the housing, and constant force expansion means disposed outside the passive container means and secured to the housing for automatically expanding the passive container means from at least a partially collapsed state such that a substantially constant level of negative pressure is created within the passive container means so as to provide for the drawing of fluids therein from a portion of a body at a substantially constant rate of suction throughout the range of evacuation;

b. connecting the opening of the housing to a portion of a body from which fluids are to be drawn; and c. activating said suction device so as to draw fluids into said suction device at said substantially constant rate of suction.

* * * * *

UNITED STATES PATENT AND TRADEMARK OFFICE
CERTIFICATE OF CORRECTION

PATENT NO. : U.S. 4,278,089
DATED : July 14, 1981
INVENTOR(S) : CHARLES M. HUCK ET AL.

It is certified that error appears in the above—identified patent and that said Letters Patent is hereby corrected as shown below:

Column 9, line 43, "claim 8" should read --claim 9--.

Signed and Sealed this

Twenty-second Day of September 1981

[SEAL]

Attest:

GERALD J. MOSSINGHOFF

Attesting Officer        Commissioner of Patents and Trademarks